(12) United States Patent
Qiu et al.

(10) Patent No.: US 6,528,091 B1
(45) Date of Patent: *Mar. 4, 2003

(54) CONTROLLED RELEASE FORMULATION OF DIVALPROEX SODIUM

(75) Inventors: Yihong Qiu, Gurnee, IL (US); Paul Richard Poska, Mundelein, IL (US); Howard S. Cheskin, Glencoe, IL (US); J. Daniel Bollinger, Libertyville, IL (US); Robert K. Engh, Kenosha, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/143,559

(22) Filed: May 10, 2002

Related U.S. Application Data (63) Continuation of application No. 09/216,650, filed on Dec. 18, 1998, now Pat. No. 6,419,953.

(51) Int. Cl.[7] .............................. A61K 9/20; A61K 9/14; A61K 9/50; A61K 9/26
(52) U.S. Cl. ...................... 424/465; 424/464; 424/489; 424/499; 424/468; 424/470
(58) Field of Search ................................. 424/465, 464, 424/489, 499, 468, 470

(56) References Cited

U.S. PATENT DOCUMENTS

| | | |
|---|---|---|
| 4,369,172 A | 1/1983 | Schor et al. |
| 4,699,927 A | 10/1987 | Deboeck |
| 4,913,906 A | 4/1990 | Friedman et al. |
| 4,988,731 A | 1/1991 | Meade |
| 5,009,897 A | 4/1991 | Brinker et al. |
| 5,017,613 A | 5/1991 | Aubert et al. |
| 5,019,398 A | 5/1991 | Daste |
| 5,055,306 A | 10/1991 | Barry et al. |

(List continued on next page.)

FOREIGN PATENT DOCUMENTS

| | | |
|---|---|---|
| EP | 0 141 267 B1 | 8/1987 |
| EP | 0 430 287 B2 | 6/1991 |
| WO | WO 94/27587 | 12/1994 |
| WO | WO 00/37055 | 6/2000 |
| WO | WO 00/45793 A1 | 8/2000 |

OTHER PUBLICATIONS

Bialer et al., Int. J. Pharmaceutics, 20: 53–63 (1984).
Bialer et al., Biopharmaceutics and Drug Disposition, 6: 401–411 (1985).
Bialer et al., Israel J. Med. Sci., 20: 46–49 (1984).

(List continued on next page.)

*Primary Examiner*—Thurman K. Page
*Assistant Examiner*—Isis Ghali
(74) *Attorney, Agent, or Firm*—Paul D. Yasger

(57) ABSTRACT

A controlled release tablet formulation which permits once daily dosing in the treatment of epilepsy comprises from about 50 weight percent to about 55 weight percent of an active ingredient selected from the group consisting of valproic acid, a pharmaceutically acceptable salt or ester of valproic acid, divalproex sodium, and valpromide; from about 20 weight percent to about 40 weight percent hydroxypropyl methylcellulose; from about 5 weight percent to about 15 weight percent lactose, from about 4 weight percent to about 6 weight percent microcrystalline cellulose, and from about 1 weight percent to about 5 weight percent silicon dioxide having an average particle size ranging between about 1 micron and about 10 microns; all weight percentages based upon the total weight of the tablet dosage form. Also disclosed are pre-tableting granular formulations, methods of making the granular formulations and tablets, and a method of treating epilepsy employing the controlled release tablet formulations of the invention.

2 Claims, 4 Drawing Sheets

U.S. PATENT DOCUMENTS

| | | | |
|---|---|---|---|
| 5,169,642 | A | 12/1992 | Brinker et al. |
| 5,185,159 | A | 2/1993 | Aubert et al. |
| 5,212,326 | A | 5/1993 | Meade |
| 5,589,191 | A | 12/1996 | Ukigaya et al. |
| 6,077,542 | A | 6/2000 | Sherman |
| 6,150,410 | A | 11/2000 | Engh et al. |

OTHER PUBLICATIONS

Collins et al., Extended Release Formulations of Anticonvulsant Medications Clinical Pharmacokinetics and Therapeutic Advantages, CNS Drugs Sep. 14, 2000 (3): 203–212.

Freitag, et al., "Depakote ER in Migraine Prophylaxis", Abstract No. S07.003, Nuerology 54 Apr. 2000 (Suppl 3), p. A14.

*Physicians' Desk Reference*, (Web Version), 2001, Depakote ER, published by The Medical Economics Company.

Abstract of Collins, et al., "Extended Release Formulations of Anticonvulsant Medications Clinical Pharmacokinetics and Therapeutic Advantages", CNS Drugs, New Zealand, 2000, 14/3 (203– 212).

Abstract of Bialer, et al., "Criteria to Assess in Vivo Performance and Bioequivalence of Generic Controlled–Release Formulations of Carbamazepine", Epilepsia, United States, 1998, 39/5 (513–519).

Abstract of Chun, et al., "Multiple–dose Evaluation of the Absorption Characteristics of Divalproex Sodium Tablets, a Delayed–Release Preparation of Valproate, in Healthy Volunteers", Clinical Drug Investigation, New Zealand, 1995, 10/1 (40–47).

Abstract of Bressolle, et al., "A Double Weibull Input Function Describes the Complex Absorption of Sustained–Release Oral Sodium Valproate", Journal of Pharmaceutical Sciences, United States, 1994, 83/10 (1461–1464).

Abstract of Hussein, et al., "Pharmacokinetics of Valproate after Multiple– dose Oral and Intravenous Infusion Administration: Gastrointestinal–related Diurnal Variation", Journal of Clinical Pharmacology, United States, 1994, 34/7 (754–759).

Abstract of Wilder, et al., "Gastrointestinal Tolerance of Divalproex Sodium", Neurology, United States, 1983, 33/6 (808–811).

Abstract of Wilder, et al., "Twice–daily Dosing of Valproate with Divalproex", Clinical Pharmacology and Therapeutics, United States, 1983, 34/4 (501–504).

Colins, et al., "Depakote CR: Biopharmaceutical and Pharmacokinetic Studies of a New Formulation for Once Daily Dosing", Neurology, vol. 50(4), Supplement 4, Apr. 1998, p. A426.

Samara, et al., "Bioavailability of a Controlled–Release Formulation of Depakote", No. 3.053, Epilepsia, vol. 38, Suppl. 8, 1997.

Cavanaugh, et al., "Effect of Food on the Bioavailability of a Controlled–Release Formulation of Depakote Under Multiple–Dose Conditions", No. 2.002, Epilepsia, vol. 38, Suppl. 8, 1997.

CONTROLLED RELEASE FORMULATION OF DIVALPROEX SODIUM

This apprehension is a continuation of Ser. No. 09/216,650 filed Dec. 18, 1998 U.S. Pat. No. 6,419,953.

TECHNICAL FIELD

The present invention relates to pharmaceutical formulations. More particularly, the present invention concerns a formulation comprising valproic acid, a pharmaceutically acceptable salt, ester, or amide thereof or divalproex sodium, in a controlled release tablet formulation.

BACKGROUND OF THE INVENTION

2-Propylpentanoic acid, more commonly known as valproic acid (VPA), its amide, valpromide (VPO), and certain salts and esters of the acid are effective in the treatment of epileptic seizures or as antipsychotic agents. U.S. Pat. No. 4,988,731 to Meade discloses an oligomer having a 1:1 molar ratio of sodium valproate and valproic acid containing 4 units, and U.S. Pat. No. 5,212,326 to Meade discloses a stable, non-hygroscopic solid form of valproic acid which comprises an oligomer having 1:1 molar ratio of sodium valproate and valproic acid and containing four to six units. Divalproex sodium (sodium hydrogen divalproate) is one of the most widely accepted antiepileptic agents currently available.

However, despite its efficacy in the treatment of epilepsy, valproic acid has been shown to exhibit an elimination half-life which is shorter than other commonly used antiepileptic agents. Half-lives for the drug of between six and seventeen hours in adults and between four and fourteen hours in children have been reported. This leads to substantial fluctuations in the plasma concentration of the drug, especially in chronic administration. To maintain reasonably stable plasma concentrations, it is necessary to resort to frequent dosing, and the resulting inconvenience to the patient often results in lowered compliance with the prescribed dosing regimen. Moreover, widely fluctuating plasma concentrations of the drug may result in administration of less than therapeutic amounts of the drug in a conservative dosing regimen, or amounts too large for the particular patient in an aggressive dosing regimen.

To overcome this disadvantage, a concerted effort has been devoted to the discovery of valproic acid formulations which will maintain more constant plasma levels of the drug following administration. The ultimate goal of these studies has been the discovery of a formulation which affords stable plasma levels in a once-a-day dosing regimen. These efforts fall generally into one of two categories: (a) finding a form of the active ingredient which is more slowly released to the body metabolically, and (b) finding a formulation which delivers the drug by either a timed- or controlled-release mechanism.

U.S. Pat. No. 4,369,172 to Schor, et al. describes, for example, a prolonged release therapeutic composition based on mixtures of hydroxypropyl methylcellulose, ethyl cellulose and/or sodium carboxymethyl cellulose. The patentees provide a long list of therapeutic agents which they suggest can be incorporated into the formulation including sodium valproate.

U.S. Pat. No. 4,913,906 to Friedman, et al. discloses a controlled release dosage form of valproic acid, its amide, or one of its salts or esters in combination with a natural or synthetic polymer, pressed into a tablet under high pressure.

U.S. Pat. No. 5,009,897 to Brinker, et al. discloses granules, suitable for pressing into tablets, the granules comprising a core of divalproex sodium and a coating of a mixture of a polymer and microcrystalline cellulose.

U.S. Pat. No. 5,019,398 to Daste discloses a sustained-release tablet of divalproex sodium in a matrix of hydroxypropyl methylcellulose and hydrated silica.

U.S. Pat. No. 5,055,306 to Barry, et al. discloses an effervescent or water-dispersible granular sustained release formulation suitable for use with a variety of therapeutic agents. The granules comprise a core comprising the active ingredient and at least one excipient, and a water insoluble, water-swellable coating comprising a copolymer of ethyl acrylate and methyl methacrylate and a water soluble hydroxylated cellulose derivative. The patentees suggest a list of therapeutic agents which may be used in the formulation of the invention, including sodium valproate.

U.S. Pat. No. 5,169,642 to Brinkler, et al. discloses a sustained release dosage form comprising granules of divalproex sodium or amides or esters of valproic acid coated with a sustained release composition comprising ethyl cellulose or a methacrylic methyl ester, a plasticizer, a detackifying agent, and a slow-release polymeric viscosity agent.

U.S. Pat. No. 5,185,159 to Aubert, et al. discloses a formulation of valproic acid and sodium valproate which is prepared without the use of either a binder or a granulating solvent. The formulation optionally contains precipitated silica as an anti-sticking or detackifying agent.

U.S. Pat. No. 5,589,191 to Exigua, et al. discloses a slow release sodium valproate tablet formulation in which the tablets are coated with ethyl cellulose containing silicic acid anhydride.

Published PCT application WO 94/27587 to Ayer, et al. discloses a method for control of epilepsy by delivering a therapeutic composition of valproic acid or a derivative in combination with a poly(alkylene oxide).

Bialer, et al., "Metabolism of Antiepileptic Drugs," pp. 143–151, R. H. Levy, Ed., Raven Press, New York, 1984; Int. J. Pharmaceutics, 20: 53–63 (1984); and Biopharmaceutics and Drug Disposition, 6: 401–411 (1985); and Israel J. Med. Sci., 20: 46–49 (1995) report the pharmacokinetic evaluation of several sustained release formulations of valproic acid.

There remains, however, the need for a sustained release formulation of valproic acid which will effectively maintain plasma concentrations of the drug at more constant levels.

SUMMARY OF THE INVENTION

The present invention provides, in its principal embodiment, a controlled release tablet dosage form comprising from about 50 weight percent to about 55 weight percent of an active ingredient selected from the group consisting of valproic acid, a pharmaceutically acceptable salt or ester of valproic acid, divalproex sodium, and valpromide; from about 20 weight percent to about 40 weight percent hydroxypropyl methylcellulose; from about 5 weight percent to about 15 weight percent lactose, from about 4 weight percent to about 6 weight percent microcrystalline cellulose, and from about 1 weight percent to about 5 weight percent silicon dioxide having an average particle size ranging between about 1 micron and about 10 microns; all weight percentages based upon the total weight of the tablet dosage form.

The tablet provides the active pharmaceutical in a hydrophilic matrix which slowly releases the active agent over a prolonged period of time in such a manner as to provide substantially level plasma concentrations of the drug following once-a-day dosing.

In an alternative embodiment, the present invention provides a dry granular composition suitable for compressing into a tablet dosage form, the granular composition comprising particles of a size smaller than about I mm comprising from about 50 weight percent to about 55 weight percent of an active ingredient selected from the group consisting of valproic acid, a pharmaceutically acceptable salt or ester of valproic acid, divalproex sodium, and valpromide; from about 20 weight percent to about 40 weight percent hydroxypropyl methylcellulose; from about 5 weight percent to about 15 weight percent lactose, from about 4 weight percent to about 6 weight percent microcrystalline cellulose, and from about 1 weight percent to about 5 weight percent silicon dioxide having an average particle size ranging between about 1 micron and about 10 microns; all weight percentages based upon the total weight of the granular composition.

In a further embodiment, the present invention provides a granular composition suitable for pressing into a controlled release tablet dosage form comprising the steps of a) dry blending a mixture of from about 50 weight percent to about 55 weight percent divalproex sodium, from about 20 weight percent to about 40 weight percent hydroxypropyl methylcellulose, and from about 5 weight percent to about 15 weight percent lactose to form a uniform mixture of the dry ingredients; b) wet granulating the dry uniform mixture from step a); c) drying and sizing the wet granules from step b) to select granules having an average size below 1 mm; and d) dry blending the granules with from about 4 weight percent to about 6 weight percent microcrystalline cellulose, and from about 1 weight percent to about 5 weight percent silicon dioxide having an average particle size ranging between about 1micron and about 10 microns, or the microcrystalline cellose can be dry blended in step (a) with the divalproex sodium, hydroxypropyl methylcellulose and lactose.

In yet another embodiment, the present invention provides a method of preparing a controlled release tablet dosage form of divalproex sodium comprising the steps of a) dry blending a mixture of from about 50 weight percent to about 55 weight percent divalproex sodium, from about 20 weight percent to about 35 weight percent hydroxypropylmethyl cellulose, from about 5 weight percent to about 15 weight percent lactose to form a uniform mixture of the dry ingredients; b) wet granulating the dry uniform mixture from step a); c) drying and sizing the wet granules from step b) to select granules having an average size below 1 mm; d) dry blending the granules with from about 4 weight percent to about 6 weight percent microcrystalline cellulose, and from about 1 weight percent to about 5 weight percent silicon dioxide having an average particle size ranging between about 1 micron and about 10 microns; and e) compressing the blended granules of step h) under a force ranging between about 2000 lbf (about $8.9 \times 10^3$ Newtons) and 10,000 lbf (about $4.45 \times 10^4$ Newtons). In a similar manner, the microcrystalline cellulose can be dry blended in step (a) with the divalproex sodium, hydroxypropyl methylcellulose and lactose.

BRIEF DESCRIPTION OF THE DRAWINGS

In the drawings, which form a part of this specification.

DETAILED DESCRIPTION

As used throughout this specification and the appended claims, the terms "sustained release," "prolonged release," and "controlled release" as applied to drug formulations have the meanings ascribed to them in "Remington's Pharmaceutical Sciences," $18^{th}$ Ed., p.1677, Mack Pub. Co., Easton, Pa. (1990). Sustained release drug systems include any drug delivery system which achieves the slow release of drug over an extended period of time, and include both prolonged and controlled release systems. If such a sustained release system is effective in maintaining substantially constant drug levels in the blood or target tissue, it is considered a controlled release drug delivery system. If, however, a drug delivery system is unsuccessful at achieving substantially constant blood or tissue drug levels, but nevertheless extends the duration of action of a drug over that achieved by conventional delivery, it is considered a prolonged release system.

The formulations of the present invention provide a controlled release formulation for valproic acid. The term "valproic acid" is meant to encompass the compound 2-propylpentanoic acid per se, and its pharmaceutically acceptable salts, and compounds which readily metabolize in vivo to produce valproic acid, such as valproic acid amide (valpromide), as well as other pharmaceutically acceptable amides and esters of the acid. A particularly preferred form of valproic acid for the compositions of the present invention is the complex formed between one mole of 2-propylpentanoic acid and its sodium salt, is commonly referred to a "divalproex sodium." Divalproex sodium is disclosed in U.S. Pat. Nos. 4,988,731 and 5,212,326 to Meade and can be represented by the following formula where m ranges from two to about six:

Experimental

One gram tablets containing 538 mg of divalproex sodium, magnesium stearate, dicalcium phosphate, microcrystalline cellulose (Avicel®. FMIC Corporation, Philadelphia Pa., USA) and/or lactose and various hydrophilic polymers were prepared. Hydrophilic polymers tested included hydroxypropyl methylcellulose, methylcellulose (Methocel® grades K100LVP CR, K4MP CR, K15MP CR and K100L MP CR, Dow Chemical, Midland, Mich. USA); hydroxypropyl cellulose (Klucel® LF, Hercules, Inc., Wilmington, Del., USA); and alginate (Keltone® grades LVCR and HVCR, Kelco Co., San Diego, Calif., USA).

Bulk drug was milled prior to use and was sized to pass a 40 mesh sieve (0.42 mm nominal mesh opening). The milled and sieved bulk drug was dry-mixed with polymer and excipients in a Collette Gral 10 high shear mixer for 5 min at a high chopper speed of 3000 rpm and impeller speed of 200 rpm. Granules were prepared by adding 70 ml/kg of granulation fluid (water or water/ethanol mixtures) to the polymer/drug/excipient powder mixture over a 1–2 minute period at high chopper speed of 3000 rpm and impeller speed of 500 rpm. Additional fluid of 10–165 ml was added in one step as needed in order to reach granulation end-point. Total granulation time ranged from 2–18 min.

Tablet matrix ingredients included microcrystalline cellulose, lactose, magnesium stearate, and silicon dioxide. The resulting granules were tray dried at 50° C.–55° C. overnight under reduced pressure. The dried granules were mixed with lubricant (magnesium stearate) in a bag and then passed through a 20 mesh (0.84 mm nominal opening) sieve. Tablets weighing 1 g were pressed in a Model C Carver Press tableting machine using a 0.747 inch (1.9 cm)×0.360 inch (0.91 cm) ovaloid die at a compression force between about 2000 lbf (about $8.9 \times 10^3$ Newtons) and about 10,000 lbf (about $4.45 \times 10^4$ Newtons), preferably between about 2300 lbf ($1.02 \times 10^4$ Newtons) to about 5000 lbf ($2.25 \times 10^4$ Newtons). The tablet compositions are presented in Table 1.

withdrawn and filtered through a 0.45 μm filter and assayed by TDX® fluorescent polarization immunoassay. Upon withdrawal of each sample, an equal volume of medium was added to the test mixture to maintain constant volume. The test conditions were as follows:

| | |
|---|---|
| Apparatus | USP II, paddle |
| Medium | 1M HCl for one hour; remaining time pH 6.8 buffer |
| Volume of medium | 900 ml |
| Temperature | 37° C. = 0.5° C. |
| Paddle speed | 100 rpm |
| Sampling volume | 1.5 ml |
| Sampling times | 0, 0.5, 1, 2, 4, 6, 8, 13, 24 hours |

The results of these tests are presented in Table 2.

Based upon these initial studies, and the data appearing in Table 2 above, the following conclusions were drawn:

(1) Effects on tablet hardness: The use of ethanol as a granulation fluid tends to increase tablet hardness. There is a strong interaction between ethanol and particle size of the bulk drug. The increase in hardness was only observed for formulations containing drug of larger particle size. The opposite effect was found for drug of smaller particle size.

TABLE 1

Test Divalproex Matrix Tablet Formulations

| Ingredient[1] | A | B | C | D | E | F | G | H | I |
|---|---|---|---|---|---|---|---|---|---|
| Divalproex sodium | 50 | 50 | 50 | 50 | 50 | 53.8 | 53.8 | 53.8 | 53.8 |
| Methocel ® K100LVPCR | 18 | 20 | — | — | — | — | — | — | 10 |
| Methocel ® K4MPCR | 8 | — | — | — | — | — | — | — | — |
| Klucel ® LF | — | 20 | — | — | — | — | — | — | — |
| Keltone ® HVCR | — | — | 30 | — | — | — | — | — | — |
| Methocel ® K15MPCR | — | — | — | — | 30 | 26 | 35 | — | 16 |
| Methocel ® K100MPCR | — | — | — | 15 | — | — | — | 30 | — |
| Lactose | 23 | 9.5 | 9.5 | 29.5 | 14.5 | 14.7 | 5.7 | 10.7 | 14.7 |
| Avicel ® PH101 | — | 0 | 5 | 5 | 5 | 5 | 5 | 5 | 5 |
| PVP[2] | — | — | 5 | — | — | — | — | — | — |
| Magnesium Stearate | 1 | 0.5 | 0.5 | 0.5 | 0.5 | 0.5 | 0.5 | 0.5 | 0.5 |

[1]Percent by weight, based upon the total tablet weight
[2]Poly(vinylpyrrolidone)

Initial Formulation Screening

Initial screening of the matrix tablet formulations was performed using a number of tests. Tablet hardness for each formulation was measured using a Model VK2000 VanKel tablet hardness analyzer and recorded in units of kiloPascals (kP) as the average of ten trials.

Friability of the tablets were tested by rotating the tablets samples 100 times using a Erweka TA friabilator. Friability of tablets for each formulation were calculated based on the weight loss of the tablets in this test.

Bulk density of the formulation granules was measured by carefully filling a glass graduated cylinder to the 100 ml mark. Tap density was determined following 100 taps of the filled cylinder.

Determination of granule size distribution was performed by collecting granules larger than 140 mesh (about 0.105 mm nominal mesh opening) and 40 mesh (about 0.42 mm nominal mesh opening) for evaluation of the percentage of fines and large granules.

In vitro dissolution tests were conducted using Apparatus II described in the *United State Pharmacopeia* XXI/*National* Formulary XVI. Samples aliquots of 1.5 ml were (2) Effects on friability: The use of drug having a small particle size reduced friability. However, this effect was significant only for formulations using water as granulation fluid.

(3) Effects on density: The use of ethanol as a granulation fluid was shown to decrease the density of the granules. However, significant interactions of ethanol with the use of Klucel®, and of ethanol with drug particle size were observed. Ethanol decreased the density only of formulations containing drug of larger particle size and/or formulations without Klucel® present. The opposite effects were found for formulations containing smaller drug particles and/or Klucel®. The same conclusions were obtained with either tap or bulk density as response.

(4) Effects on size of granules: More granules of larger size were obtained with the use of drug having a larger particle size. Moreover, interaction between ethanol and Klucel® was found to be significant i.e. use of ethanol tends to generate larger granules when there is no Klucel® present in the formulation. No effect was observed for formulations containing 4% Klucel®. Factors that showed significant influences on the percentage of fines in the granules included ethanol, drug particle size, and their interaction. Using smaller drug particles tended to yield more fines in the granules. More fines were generated when ethanol was used as a granulation fluid. The effect of ethanol was most significant for formulations containing drug of a small particle size.

(5) Effects on granulation fluid volume: In order to obtain granulation end-point, more fluid volume was needed for formulations containing either drug of a smaller particle size or with the use of ethanol as granulation fluid.

Figure 1:
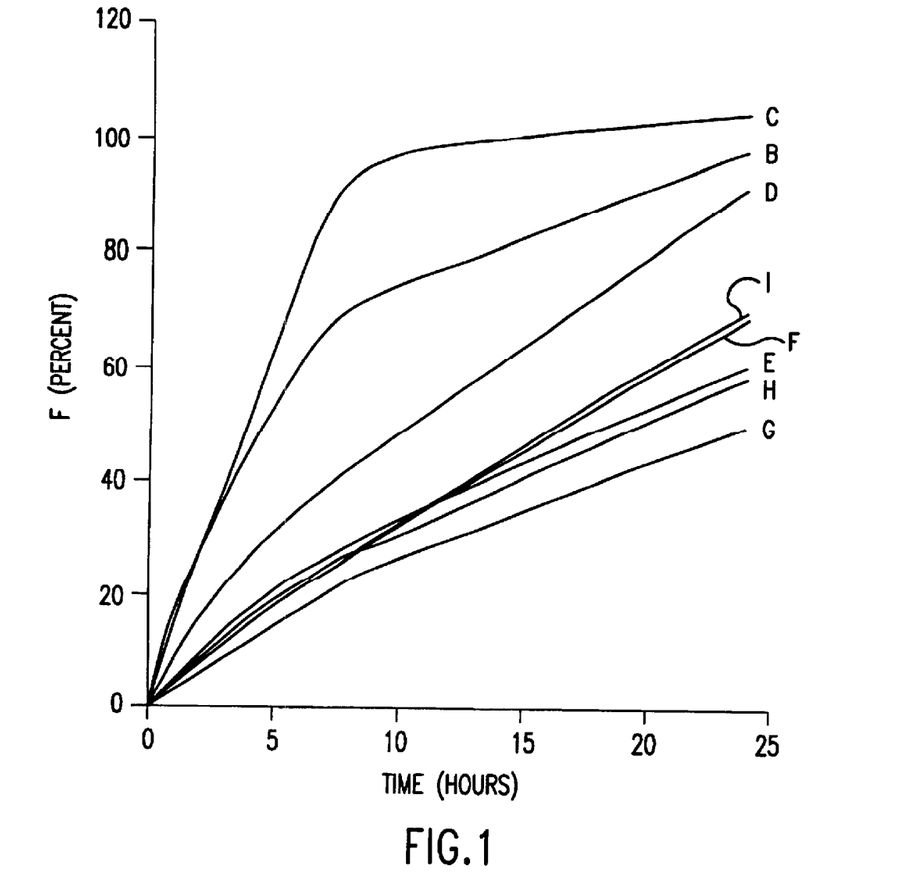
FIG. 1 is a graphical representation of the release of drug from several test controlled release tablet formulations under in vitro conditions.

(6) In vitro drug release: In vitro percent release of valproic acid from controlled-release tablets are shown in FIG. 1. The difference in release profiles among formulations was small. In the study, percent release at 8 hours ($Q_{8hr}$) was used to represent release rate for data analysis. It was found that the use of Klucel® or drug of a larger particle size in the formulation resulted in an increase in release rate. Similar results were obtained when $Q_{10hr}$ or $Q_{24hr}$ was used to estimate the release rate.

Formulations containing high load and high viscosity grades of polymers often showed poor compressibility. This is believed to be the result of the increase in polymer order and elasticity with increasing molecular weight. Hardness of the tablets remained almost unchanged under compression forces ranging from about 3000 lb ($1.3 \times 10^4$ Newtons) to about 10,000 lb ($4.45 \times 10^4$ Newtons).

TABLE 2

| Formulation | Granulating Fluid Volume | Hardness (kP) | Friability (% Loss) | Tap Density (g/ml) | Bulk Density (g/ml) | % Granule Size >40 Mesh | Fines[1] | $Q_{8\ hr}$ (%)[2] |
|---|---|---|---|---|---|---|---|---|
| A | 100 | 11.9 | 0.049 | 0.504 | 0.429 | 22.6 | 6.1 | 27.6 |
| B | 80 | 7.2 | 0.16 | 0.515 | 0.438 | 31.3 | 9.8 | 29.0 |
| C | 115 | 12.2 | 0.025 | 0.459 | 0.39 | 30.2 | 3.3 | 28.6 |
| D | 80 | 8.4 | 0.162 | 0.459 | 0.406 | 38.2 | 6.6 | 30.4 |
| E | 235 | 10.4 | 0.060 | 0.599 | 0.509 | 21.5 | 40.7 | 27.0 |
| F | 110 | 12.2 | 0.006 | 0.400 | 0.340 | 49.2 | 1.8 | 28.0 |
| G | 200 | 9.4 | 0.085 | 0.596 | 0.506 | 24.0 | 29.7 | 29.7 |
| H | 150 | 12.9 | 0.142 | 0.593 | 0.504 | 35.0 | 22.8 | 30.0 |
| I | 130 | 9.5 | 0.015 | 0.475 | 0.404 | 33.8 | 1.2 | 28.8 |

[1]Defined as percent granules passing a 0.105 mm nominal mesh opening
[2]Defined as percent drug released in an 8-hour period under the in vitro test conditions In order to increase the hardness of tablets, microcrystalline cellulose and colloidal silicon dioxide were tested by externally adding small amounts to the granules at levels of 1–5%. Table 3 shows the results from the test. It was found that external addition of small amounts of microcrystalline cellulose or colloidal silicon dioxide significantly increased tablet hardness.

TABLE 3

Effect of External Addition of Microcrystalline Cellulose or Silicon Dioxide

| Hardness Test Formulation | Additive | Hardness (kP) |
|---|---|---|
| Ia | None | 6.2 |
| Ib | 5% Avicel ® | 9.6 |
| Ic | 5% Avicel ® and 1% silicon dioxide[1] | 13.8 |
| IIa | None | — |
| IIb | 1% Silicon dioxide[1] | 10.9 |
| IIc | 5% Avicel ® and 1% silicon dioxide[1] | 14.4 |
| IIIa | None | 5.8 |
| IIIb | 1% Silicon dioxide[1] | 10.8 |
| IIIc | 5% Avicel ® and 1% silicon dioxide[1] | 14.8 |

[1]Silicon dioxide was Cab-O-Sil M-5 fumed silica (Cabot Corp., Boyertown, PA, USA) having average particle size of between about 0.2 and 0.3 microns As shown by the data in Table 3, the addition of either 1% silicon dioxide or 5% microcrystalline cellulose to the hydrophilic matrix formulations of the invention almost doubled tablet hardness, while adding both resulted in a greater than doubling of tablet hardness. However, although the results shown above demonstrated improvement of tablet hardness by the combined use of the external addition of Avicel® microcrystalline cellulose and Cab-o-sil® silicon dioxide, problems of sticking and relatively low density persisted. The low bulk density (i.e. 40 g/l) of the small particle size Cab-O-Sil® fumed silica led to the problem of not being able to load sufficient material into the tablet die.

In response to this problem, a different silicon dioxide having a larger average particle size ranging from about 1 micron to about 10 microns, preferably ranging between about 2 microns to about 5 microns, and most preferably about 2–3 microns was used. One such material is available as Syloid® 244, available from W. R. Grace, Lexington, Mass., USA. When this material was used, initially intended as a de-tackifying and hardening agent for tableting, a surprising and unexpected benefit was conferred upon the formulation, as shown below. The material was added "externally" to the formulation: that is, the active ingredient, polymer(s) and excipients were dry blended, wet granulated, and then dried and sized. The silicon dioxide was then added to the granular formulation and the resulting mixture blended prior to pressing into tablets.

Figure 2:
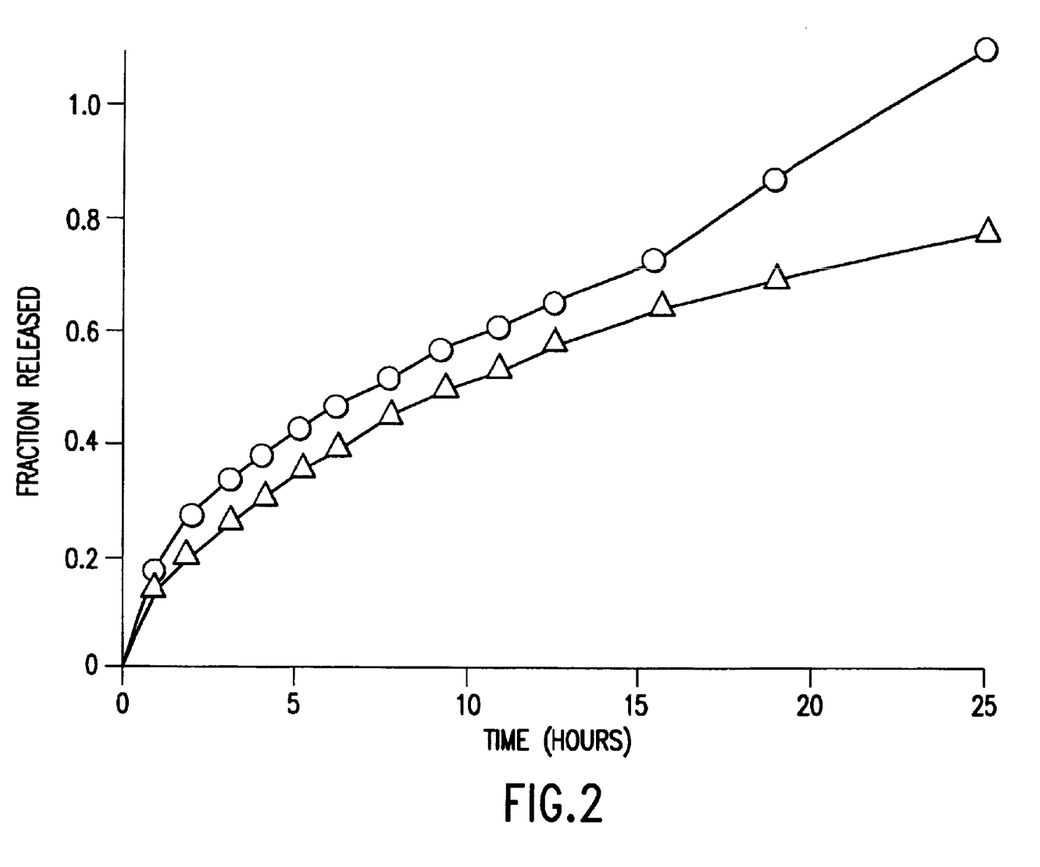
FIG. 2 is a graphical representation of in vitro release of drug from two preferred controlled release tablet formulations of the invention.

On the basis of the above findings, preferred tablet formulations were chosen for an in vivo absorption study in healthy human subjects. The ingredients of the formulations and in vitro release rates are shown in Table 4 and FIG. 2, respectively. The formulations were designed to have different release rates by using high viscosity HPMC alone or blended with low viscosity HPMC. The target in vitro release rates were chosen to release drug in vivo for 16–20 hours.

Figure 3:
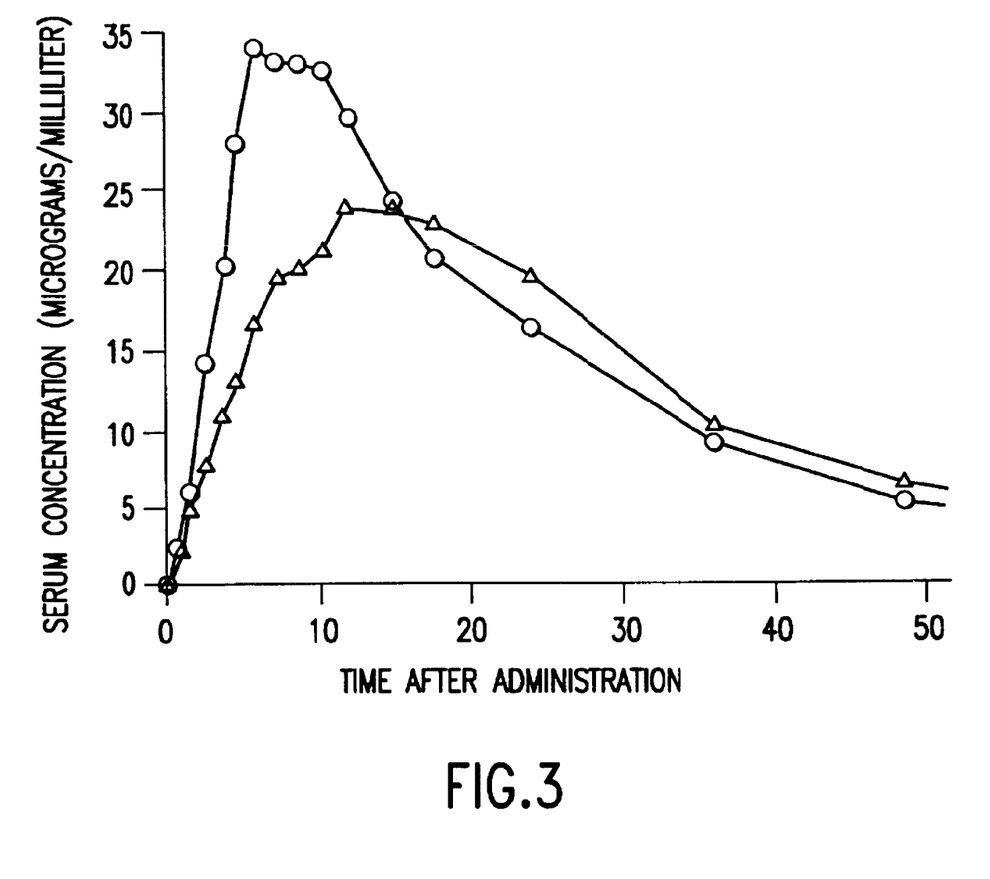
FIG. 3 is a graphical representation of plasma concentration in human subjects following administration of two of the preferred controlled release tablet formulations of the invention.
Figure 4:
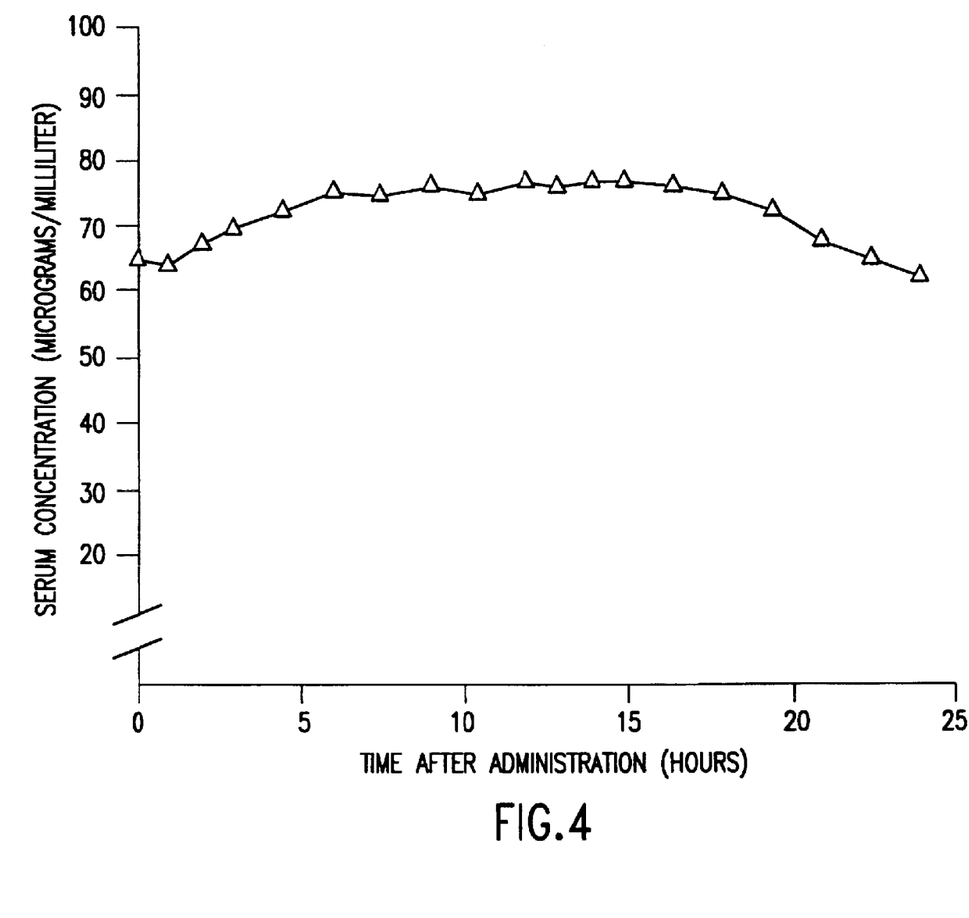
FIG. 4 is a graph showing plasma concentrations of valproic acid in a human subject following multiple administrations of a preferred controlled release formulation of the invention.

Using the two preferred formulations described in Table 4. two in vivo studies in human subjects were carried out. FIG. 3 shows the mean plasma concentration-time profiles of valproic acid in humans following a single oral dose of the two formulations. It was found that preferred formulations A and B provided prolonged absorption of valproic acid for approximately 10 hours and 24 hours respectively. It was apparent that the slower releasing formulation, tablet B, showed more desirable sustained plasma levels. Therefore, this formulation was further tested in a multiple dose study in healthy human subjects at an oral dose of 1 gram given once daily. The results shown in FIG. 4 indicated that mean steady-state plasma levels were well controlled between 62.3 and 78.2 μg/ml with minimal fluctuation, which falls within the therapeutic range of valproic acid (30–100ug/ml).

TABLE 4

Preferred Controlled Release Formulations of the Invention

| Ingredient | Preferred Formulation A | Preferred Formulation B |
|---|---|---|
| Divalproex sodium (milled)[1] | 53.82%[2] | 53.82% |
| Hydroxypropyl methylcellulose (Methocel ® K15M, CR) | 8% | 30% |
| Methyl cellulose (Methocel ® K100L, CR) | 18% | — |
| Anhydrous lactose | 12.18% | 8.18% |
| Microcrystalline cellulose (Avicel ® PH 101) | 5% | 5% |
| Silicon dioxide (Average particle size 1 μm< >10 μm) | 3% | 3% |

TABLE 4-continued

Preferred Controlled Release Formulations of the Invention

| Ingredient | Preferred Formulation A | Preferred Formulation B |
|---|---|---|
| (Syloid ® 244) | | |
| Total tablet weight | 1 g | 1 g |

[1]Bulk drug sized to pass a 40 mesh sieve (0.42 mm nominal mesh opening
[2]All percentages in the Table expressed as weight percentages based upon the total weight of the tablet The controlled release tablet formulations of the present invention thus provide an effective delivery system for the once daily administration of valproic acid (divalproex sodium) to patients in need of such treatment. The formulations of the invention provide substantially level plasma concentrations of valproic acid falling within the therapeutic range of the drug over a period which permits administration once daily.

While there have been shown and described what are the preferred embodiments of the invention, one skilled in the pharmaceutical formulation art will appreciate that various modifications in the formulations and process can be made without departing from the scope of the invention as it is defined by the appended claims.

We claim:
1. A method of treating epilepsy comprising administering once daily to a patient in need of such treatment a controlled release tablet dosage form comprising a daily therapeutic dose of divalproex sodium from about 50 to 55 weight percent in a hydrophilic matrix comprising:
   a) from about 20 weight percent to about 40 weight percent hydroxypropyl methylcellulose;
   b) from about 5 weight percent to about 15 weight percent lactose;
   c) from about 4 weight percent to about 6 weight percent microcrystalline cellulose; and
   d) from about 1 to about 5 weight percent silicon dioxide having an average particle size ranging between about 1 micron and about 10 microns;
   all weight percentages based upon the total weight of the tablet dosage form.
2. The method of claim 1 wherein said silicon dioxide has an average particle size ranging between about 2 microns and about 5 microns.

* * * * *

UNITED STATES PATENT AND TRADEMARK OFFICE
CERTIFICATE OF CORRECTION

PATENT NO.     : 6,528,091 B1
DATED          : March 4, 2003
INVENTOR(S)    : Yihong Qiu et al.

It is certified that error appears in the above-identified patent and that said Letters Patent is hereby corrected as shown below:

<u>Title page,</u>
Item [75], Inventors, replace "Paul Richard Poska" with -- Richard Paul Poska --.

Signed and Sealed this

Twelfth Day of August, 2003

JAMES E. ROGAN
*Director of the United States Patent and Trademark Office*